United States Patent
Peytavi

(10) Patent No.: US 8,444,934 B2
(45) Date of Patent: May 21, 2013

(54) REMOVABLE MICROFLUIDIC FLOW CELL

(75) Inventor: Regis Peytavi, St-Romuald (CA)

(73) Assignee: Universite Laval, Quebec, Quebec (CA)

( * ) Notice: Subject to any disclaimer, the term of this patent is extended or adjusted under 35 U.S.C. 154(b) by 915 days.

(21) Appl. No.: 10/593,990

(22) PCT Filed: Mar. 29, 2005

(86) PCT No.: PCT/CA2005/000458
§ 371 (c)(1),
(2), (4) Date: Feb. 2, 2007

(87) PCT Pub. No.: WO2005/093388
PCT Pub. Date: Oct. 6, 2005

(65) Prior Publication Data
US 2009/0023610 A1    Jan. 22, 2009

Related U.S. Application Data

(60) Provisional application No. 60/556,372, filed on Mar. 26, 2004.

(51) Int. Cl.
*B01J 19/00* (2006.01)

(52) U.S. Cl.
USPC ........... 422/506; 422/500; 422/501; 422/502; 422/504; 422/507; 422/50; 422/402; 422/68.1; 422/72; 506/6; 494/16; 494/17; 494/23; 494/27; 494/29; 137/803; 137/814

(58) Field of Classification Search
USPC .................. 422/68.1, 72, 500–504, 506, 507, 422/50, 402; 436/177; 494/16, 17, 23, 27, 494/29, 31, 32, 33, 34; 355/220; 210/512.1; 137/803, 814; 506/6
See application file for complete search history.

(56) References Cited

U.S. PATENT DOCUMENTS 4,788,154 A * 11/1988 Guigan ........................... 422/72
5,869,004 A * 2/1999 Parce et al. .................... 422/100
(Continued)

FOREIGN PATENT DOCUMENTS

WO        97/21090 A1    6/1997
WO     WO 01/35088       5/2001
(Continued)

OTHER PUBLICATIONS

Anderson, J. et al. "Fabrication of Topologically Complex Three-Dimensional Microfluidic Systems in PDMS by Rapid Prototyping." Anal. Chem. 72. 2000. pp. 3158-3164.

(Continued)

*Primary Examiner* — In Suk Bullock
*Assistant Examiner* — Sharon Pregler
(74) *Attorney, Agent, or Firm* — Ladas & Parry LLP

(57) ABSTRACT

A microfluidic flow cell for removably interfacing with a removable-member for performing a reaction therebetween. The microfluidic flow cell device comprises at least one reaction portion defining with the removable-member a reaction chamber when in an interfaced position thereof. The microfluidic flow cell comprises at least one fluid-receiving portion for receiving a fluid therein and being in fluid communication with the reaction chamber. When the microfluidic flow cell and the removable-member are in the interfaced position, the cell is adapted to allow for the fluid in the fluid-receiving portion to flow to the reaction chamber. Devices, systems and methods comprising this microfluidic flow cell are also disclosed.

24 Claims, 7 Drawing Sheets

U.S. PATENT DOCUMENTS

| | | | |
|---|---|---|---|
| 5,922,288 A * | 7/1999 | Herst | 422/101 |
| 6,099,803 A | 8/2000 | Ackley et al. | |
| 6,245,508 B1 | 6/2001 | Heller et al. | |
| 6,258,606 B1 | 7/2001 | Kovacs | |
| 6,878,255 B1 * | 4/2005 | Wang et al. | 435/6 |
| 2002/0068357 A1 * | 6/2002 | Mathies et al. | 435/287.2 |
| 2002/0142470 A1 | 10/2002 | Clarke et al. | |
| 2003/0087292 A1 * | 5/2003 | Chen et al. | 435/6 |
| 2005/0277125 A1 * | 12/2005 | Benn et al. | 435/6 |

FOREIGN PATENT DOCUMENTS

| | | |
|---|---|---|
| WO | 02/072264 A1 | 9/2002 |
| WO | WO 03/015923 | 2/2003 |
| WO | WO 03/052428 | 6/2003 |

OTHER PUBLICATIONS

Bousse, L., et al. "Electrokinetically Controlled Microfluidic Analysis Systems." Annu. Rev. Biophys. Biomol. Struct. 29. 2000. pp. 155-181.

Madou, M., et al. "A novel design on a CD disc for 2-point calibration measurement." Sensors and Actuators 91(3). 2001. pp. 301-306.

Capanu, M., et al. "Design, Fabrication, and Testing of a Bistable Electromagnetically Actuated Microvalve." Journal of Microelectromechanical Systems. vol. 9, No. 2. Jun. 2000. pp. 181-189.

Howbrook, D., et al. "Developments in microarray technologies." Drug Discovery Today vol. 8, No. 14. 2003. pp. 642-651.

Kusnezow, W., et al. "Solid supports for microarray immunoassays." J. Mol. Recogni. 16. 2003. pp. 165-176.

Maughan, N., et al. "An introduction to arrays." Journal of Pathology. 195. 2001. pp. 3-6.

Wang, Y., et al. "Microarrays Assembled in Microfluidic Chips Fabricated from Poly(methyl methacrylate) for the Detection of Low-Abundant DNA Mutations." 75. 2003. pp. 1130-1140.

Bryant, P., et al. "Chips with everything: DNA microarrays in infectious diseases." Lancet Infect. Dis. vol. 4. Feb. 2004. pp. 100-111.

Heller, M. "DNA Microarray Technology: Devices, Systems and Applications." Annu. Rev. Biomed. Eng. 4. 2002. pp. 129-153.

Pirrung, M. "How to Make a DNA Chip." Angew. Chem. Int. Ed. 41. 2002. pp. 1276-1289.

Mikhailovich, et al. "Identification of Rifampin-Resistant *Mycobacterium tuberculosis* Strains by Hybridization, PCR, and Ligase Detection Reaction on Oligonucleotide Microchips." Journal of Clinical Microbiology. 39. Jul. 2001. pp. 2531-2540.

Chizhikov, V., et al. "Microarray Analysis of Microbial Virulence Factors." Applied and Environmental Microbiology. 67. Jul. 2001. pp. 3258-3263.

Chizhikov, V., et al. "Detection and Genotyping of Human Group A Rotaviruses by Oligonucleotide Microarray Hybridization." Journal of Clinical Microbiology. 40. pp. 2398-2407, Jul. 2002.

Wang, R., et al. "Design and evaluation of oligonucleotide-microarray method for the detection of human intestinal bacteria in fecal samples." FEMS Microbiol. Lett. 213. 2002. pp. 175-182.

Loy, A., et al. "Oligonucleotide Microarray for 16S rRNA Gene-Based Detection of All Recognized Lineages of Sulfate-Reducing Prokaryotes in the Environment." Applied and Environmental Microbiology. 68. 2002. pp. 5064-5081.

Wilson, W., et al. "Sequence-specific identification of 18 pathogenic microorganisms using microarray technology." Mol. Cell. Probes. 16. 2002. pp. 119-127.

Weidenhammer, E., et al. "Multiplexed, Targeted Gene Expression Profiling and Genetic Analysis on Electronic Microarrays." Clinical Chemistry. 48. 2002. pp. 1873-1882.

Westin, L., et al. "Antimicrobial Resistance and Bacterial Identification Utilizing a Microelectronic Chip Array." Journal of Clinical Microbiology. 39. 1097-1104, Mar. 2001

Lenigk, R., et al. "Plastic biochannel hybridization devices: a new concept for microfluidic DNA arrays." Anal. Biochem. 311. 2002. pp. 40-49.

Fan, Z., et al. "Dynamic DNA Hybridization on a Chip Using Paramagnetic Beads." Analytical Chemistry. vol. 71, No. 21. 1999. pp. 4851-4859.

Noerholm, M., et al. "Polymer microfluidic chip for online monitoring of microarray hybridizations." LabChip. 4. 1999. pp. 28-37.

Unger, M., et al. "Monolithic Microfabricated Valves and Pumps by Multilayer Soft Lithography." Science. 288. 2000. 113-116.

Liu, R., et al. "Fabrication and Characterization of Hydrogel-Based Microvalves." Journal of Microelectromechanical Systems. vol. 11, No. 1. Feb. 2002. pp. 45-53.

Miller, R., et al. "A MEMS radio-frequency ion mobility spectrometer for chemical vapor detection." Sensors and Actuators. 91. 2001. pp. 301-312.

Bavykin, S., et al. "Portable System for Microbial Sample Preparation and Oligonucleotide Microarray Analysis." Applied and Environmental Microbiology. 67. 2001. 922-928.

Bekal, S., et al. "Rapid Identification of *Escherichia coli* Pathotypes by Virulence Gene Detection with DNA Microarrays." J. Clin. Microbial. 41. 2001. 2113-2125.

Duffy, D., et al. "Rapid Prototyping of Microfluidic Systems in Poly(dimethylsiloxane)." Anal. Chem. 70. 1998. pp. 4974-4984.

* cited by examiner

REMOVABLE MICROFLUIDIC FLOW CELL

FIELD OF THE INVENTION

The present invention relates generally to the field of microfluidics. More specifically, the present invention relates to a removable microfluidic flow cell that enables to drive fluids.

BACKGROUND OF THE INVENTION

Microfluidic devices for driving fluids are known in the art. These devices generally comprise a circuitry or flow network for driving fluids such as reagents to a particular reaction area or chamber. Detection of the foregoing reaction is usually burdensome since standard detection techniques cannot be used given the relative complexity of such microfluidic devices.

Microarrays involve bimolecular interactions where one partner is in solution and the other one is attached to a surface (Howbrook et al., 2003 Drug Discovery Today, 8:642-651; Kusnezow and Hoheisel, 2003, J. Mol. Recogni. 16:165-176). For positive interaction to take place, there should be an encounter between the solution phase partner and the surface phase partner. Such an encounter could be driven by several phenomena such as diffusion, electrostatic attraction, magnetic confinements, and forced or directed flow. In most conventional microarrays, diffusion is the major driving force. However, this is a slow process requiring between 3 to 16 hours (Maughan et al., 2001, J. Pathol., 195:3-6). A system using electrostatic attraction demonstrated faster hybridization on arrays made on electrodes (U.S. Pat. No. 6,099,803). However, in these systems low ionic strength solutions must be used. Wang et al. demonstrated that dynamic DNA hybridization can be achieved by flowing analytes through a microarray surface using an especially designed array combined with microfluidic circuitry (Wang et al., 2003, Anal. Chem., 75:1130-1140).

Over the last decade, DNA microarrays have become a powerful tool for genomic and proteomic research. Microarrays allow up to several thousands of nucleic acid probes to be spotted onto very small solid supports (millimeter scale); generally glass slides (Bryant et al., 2004, Lancet Infect. Dis., 4:100-111; Heller, 2002, Annu. Rev. Biomed. Eng., 4:129-153; Maughan et al., 2001, J. Pathol., 195:3-6; Pirrung, 2002, Angew. Chem. Int. Ed., 41:1276-1289).

Recent efforts were conducted to adapt the microarray technology for rapid identification of biomolecules using signal transduction; the biomolecule binds to a specific probe attached onto the solid support (Mikhailovich et al., 2001, J. Clin. Microbiol., 39:2531-2540; Chizhikov et al., 2001, Appl. Environ. Microbiol., 67:3258-3263; Chizhikov et al., 2002, J. Clin. Microbiol., 40:2398-2407; Wang et al., 2002, FEMS Microbiol. Lett., 213:175-82; Loy et al., 2002, Appl. Environ. Microbiol., 68:5064-5081; Wilson et al., 2002, Mol. Cell. Probes, 16:119-127). Such rapid identification is important for diagnostic and forensic purposes, for food and water testing as well as for rapid pathogen detection and identification. Classical-DNA microarrays such as Affymetrix's Genechip™ or custom glass-slide technology require hybridization times of up to 18 hours for nucleic acids detection. These methods are thus not fit for rapid molecular testing.

To speed up the hybridization reaction, several approaches to provide active hybridization systems, or to increase the hybridization dynamics in passive systems have been developed. Electric fields have been used to attract nucleic acid analytes onto capture probes immobilized on electrode surfaces (U.S. Pat. Nos. 6,245,508; 6,258,606; Weidenhammer et al., 2002, Clin. Chem., 48:1873-1882; Westin et al., 2001, J. Clin. Microbiol., 39:1097-1104). Such a system allows for rapid DNA hybridization (in the order of minutes), but requires expensive hybridization equipment and reader devices.

Flow-through systems, where targets flow over the probes, increase the probability of interactions between the analyte and the probe. Wang et al. disclosed the use of microfluidic circuitries associated with microarrays, and demonstrated that smaller hybridization chambers, in combination with flow-through hybridization, enhanced the hybridization kinetics (Wang et al., 2003, Anal. Chem., 75:1130-1140).

Microfluidics is an emerging technology allowing to move very small volumes in microscopic tubing adapted for different applications. Channels and chambers are microfabricated in a base of silicon, hard plastic or soft elastomers such as PDMS (Poly-dimethylsiloxane) (Bousse et al., 2000, Annu. Rev. Biophys. Biomol. Struct.; 29:155-181; Anderson et al., 2000, Anal. Chem.; 72:3158-3164). Fluid propulsion and control valves are designed to allow sequential displacement of liquids into the various segments of the circuits. Numerous microfluidic systems have been set-up for hybridization purposes using different microfluidic technologies (Wang et al., 2003, Anal. Chem., 75:1130-1140; Lenigk et al., 2002, Anal. Biochem., 311:40-49; Fan et al., 1999, Anal. Chem. 71:4851-4859). However, these technologies are complex, expensive to prototype, and require custom made systems for the arraying of bioprobes and detection of hybridization signals Noerholm et al. developed a microfluidic circuit engraved in a plastic polymer (Noerholm et al., 2004, LabChip 4:28-37). The microarray was spotted directly onto the plastic surface of the engraved hybridization chamber. Thus, this system requires a special microarray support, and consequently, cannot be read on commercially available array scanners. Spute and Adey (WO 03/05248 A1) described a three-dimensional fluidic structure for hybridization, but this system requires several layers of microfluidic structures.

Microarrays constitute a promising technology for the rapid multi-detection of nucleic acids with potential applications in all fields of genomics including microbial (e.g. bacteria, viruses, parasites and fungi) human, animal and plant genetic analysis. Currently, hybridization protocols on microarrays are slow, need to be performed by skilled personnel, and are therefore not suited for rapid diagnostic applications such as point of care testing. The merging of microfluidic and microarray technologies provides an elegant solution to automate and speed up microarray hybridization and detection. Such an association has already been described but requires a complex and expensive microfluidic platform.

There thus remains a need to provide an improved microfluidic flow cell, an improved microfluidic device, an improved microfluidic method and an improved microfluidic system.

There thus remains a need for a rapid, efficient, reliable and low cost method for performing microarray analyses.

The present invention seeks to meet these and other needs.

SUMMARY OF THE INVENTION

An object of the invention is therefore to provide an improved microfluidic flow cell, an improved microfluidic device, an improved microfluidic method and an improved microfluidic system.

More specifically, in accordance with an aspect of the present invention there is provided a microfluidic flow cell for removably interfacing with a removable-member for performing a reaction therebetween, the microfluidic flow cell comprising:

at least one reaction portion defining with the removable-member a reaction chamber when the microfluidic flow cell and the removable-member are in an interfaced position thereof; and at least one fluid-receiving portion for receiving a fluid therein and being in fluid communication with the reaction chamber;

wherein when in the interfaced position, the microfluidic flow cell is adapted to allow for the fluid in the fluid-receiving portion to flow to the reaction chamber.

In an embodiment, the microfluidic flow further comprises a conduit providing fluid communication between the fluid-receiving portion and the reaction chamber.

In an embodiment, the microfluidic flow further comprises a plurality of separate fluid-receiving portions each receiving a respective fluid, each of the separate fluid-receiving portions being in fluid communication with a common reaction chamber. In an embodiment, the microfluidic flow cell further comprises a plurality of separate conduits, each separate conduit providing fluid communication between a respective fluid-receiving portion and the common reaction chamber. In an embodiment, the plurality of separate conduits meet at a valve for fluid communication therewith, this valve being in fluid communication with the common reaction chamber. In an embodiment, the fluid communication between the reaction chamber and the valve is provided by a common channel.

In an embodiment, the reaction portion comprises a reaction cavity. In an embodiment, this cavity comprises a structure selected from the group consisting of indentations and at least one groove.

In an embodiment, the fluid-receiving portion comprises a reagent chamber, the fluid comprising a reagent.

In an embodiment, the fluid-receiving portion comprises a fluid-receiving chamber formed within the microfluidic flow cell.

In an embodiment, the fluid-receiving portion comprises a fluid-receiving cavity defining a fluid-receiving chamber with the removable-member when the microfluidic flow cell and the removable-member are in the interfaced position.

In an embodiment, the conduit is formed within the microfluidic flow cell. In another embodiment, the microfluidic flow cell further comprises a conduit cavity, the conduit-cavity defines the conduit when the microfluidic flow cell and the removable-member are in the interfaced position.

In an embodiment, the at least one of said plurality of conduits is formed within the microfluidic flow cell. In another embodiment, the at least one of the plurality of conduits is defined by a conduit in the microfluidic flow cell when the microfluidic flow cell and the removable member are in the interfaced position.

In an embodiment, the valve is formed within the microfluidic flow cell. In another embodiment, the microfluidic flow cell further comprises a valve-cavity; the valve-cavity defines the valve when the microfluidic flow cell and the removable-member are in the interfaced position.

In an embodiment, the common channel is formed within the microfluidic flow cell. In another embodiment, the microfluidic flow cell further comprises a common channel-cavity; the common channel-cavity defines the common channel when the microfluidic flow cell and the removable-member are in the interfaced position.

In an embodiment, the microfluidic flow cell further comprises a plurality of separate fluid-receiving portions, each fluid-receiving portion of the plurality being in fluid communication with a common canal, the common canal being in communication with the reaction chamber. In another embodiment, the separate fluid-receiving portions comprise a pair of elongate bores meeting at a common part of the common canal. In an embodiment, the common part comprises a valve. In another embodiment, the common canal is formed within the microfluidic flow cell. In an embodiment, the microfluidic flow cell comprises a common canal-cavity; the common canal-cavity defines the common canal when the microfluidic flow cell and the removable-member are in the interfaced position. In an embodiment, the pair of elongate bores are formed within the microfluidic flow cell. In an embodiment, the elongate bores are formed by complementary elongate bore portions, defined by the microfluidic flow cell and the removable-member when in the interfaced position. In an embodiment, the valve is formed within the microfluidic flow cell. In another embodiment, the microfluidic flow cell further comprises a valve-cavity; the valve-cavity defines the valve when the microfluidic flow cell and the removable-member are in the interfaced position.

In an embodiment, the microfluidic flow cell further comprises a dispensing portion in fluid communication with the reaction chamber. In an embodiment, the dispensing portion is in fluid communication with the external environment of said microfluidic flow cell. In an embodiment, the dispensing portion comprises a dispensing channel formed within the microfluidic flow cell. In another embodiment, the dispensing portion comprises a dispensing channel, the microfluidic flow cell further comprises a dispensing channel-cavity; the dispensing channel-cavity defines the dispensing channel when the microfluidic flow cell and the removable-member are in the interfaced position.

In an embodiment, the microfluidic flow cell comprises hydrophobic material. In another embodiment, the said microfluidic flow cell comprises a substrate. In an embodiment, the substrate comprises elastomeric material. In an embodiment, the elastomeric material comprises PDMS.

In an embodiment, the removable-member comprises a support for performing a reaction thereon. In an embodiment, this support comprises hydrophobic material. In an embodiment, the support is functionalized to allow for the binding of probes thereon. In an embodiment, the support comprises glass. In an embodiment, the support comprises a microarray. In an embodiment, the microarray comprises bioprobe spots. In an embodiment, the bioprobe spots are selected from the group consisting of DNA, RNA, oligonucleotides, oligonucleotide analogs, proteins, peptides, organic molecules, sugars, drugs and a combination thereof.

In an embodiment, the microfluidic flow cell further comprises a plurality of fluid-receiving portions and a plurality of channels in fluid communication therewith, the channels being in communication with the reaction chamber. In an embodiment, the plurality of channels access individual spots of the microarray. In an embodiment, plurality of channels access individual groups of spots of the microarray.

In an embodiment, the removable-member comprises an enclosure. In an embodiment, the enclosure comprises a removable seal.

In an embodiment, the microfluidic flow cell is adapted to be actuated so as to provide for the fluid in the fluid-receiving portion to flow to the reaction chamber. In an embodiment, this actuation is provided by forces selected from the group consisting of: gravity, centrifugation, capillary force, centripetal force, gas-pressure, electro-osmosis, DC and AC electrokinetics, electrophoresis, electrowetting, magnetic force, acoustic force, pneumatic drive force, mechanical micro-pump force, positive and negative displacement force, thermal force, electrochemical bubble generation force, and combinations thereof.

In an embodiment, the fluid is initially in dry form and is adapted to be liquefied.

In an embodiment, the microfluidic flow cell further comprises at least one vent, this vent being in fluid communication with the ambient environment and with the reaction chamber. In another embodiment, this vent is in fluid communication with the ambient environment and with the fluid-receiving portion. In another embodiment, this vent is in fluid communication with the ambient environment and with the conduit. In another embodiment, this vent is in fluid communication with the ambient environment and with the valve. In another embodiment, this vent is in fluid communication with the ambient environment and with the common channel. In another embodiment, this vent is in fluid communication with the ambient environment and with the common canal. In another embodiment, this vent is in fluid communication with the ambient environment and with the dispensing portion.

In another embodiment, the removable-member comprises an auxiliary microfluidic flow cell.

In another embodiment, the removable-member comprises a support comprising a support cavity defining said reaction chamber when in said interfacing position, said reaction cavity comprising a fluid outlet in communication with said reaction chamber.

In accordance with another aspect of the present invention, there is provided a microfluidic device comprising:

a microfluidic flow cell in combination with a removable-member;

at least one reaction chamber defined by the microfluidic flow cell and the removable-member when in an interfaced position thereof for performing a reaction therein; and at least one fluid-receiving chamber for receiving a fluid therein and being in fluid communication with the reaction chamber;

wherein the microfluidic flow device is adapted to allow for the fluid in said fluid-receiving chamber to flow to said reaction chamber.

In accordance with a further aspect of the present invention, there is provided a microfluidic system for driving fluids, the system comprising:

at least one microfluidic device comprising:

a microfluidic flow cell comprising at least one reaction portion and at least one fluid-receiving portion for receiving a fluid therein;

a removable-member for interfacing with the microfluidic flow cell as to perform a reaction therebetween;

a reaction chamber for performing a reaction therein, the reaction chamber being defined by the reaction portion when interfaced with the removable-member, the reaction chamber being in fluid communication with the fluid-receiving portion; and a force-providing device for providing an external force onto the microfluidic device so as to provide for the fluid in said fluid-receiving portion to flow to said reaction chamber.

In an embodiment, the force-providing device comprises a centrifuge device. In an embodiment, the centrifuge device comprises a rotatable platform for positioning a plurality of said microfluidic devices thereon. In an embodiment, the platform comprises microfluidic device receiving portions. In an embodiment, the microfluidic device receiving portions comprise slots, the removable member comprising a glass support slide to be received by the slot. In an embodiment, the rotatable platform comprises a disc. In an embodiment, this disc comprises a central portion for operatively communicating with an actuator to be rotated thereby. In an embodiment, this central portion comprises an opening, the actuator comprises a hub mounted to a motor. In an embodiment, the disc comprises a waste reservoir positioned near the periphery thereof. In an embodiment, the microfluidic device comprises a dispensing portion for dispensing fluid therethrough, the microfluidic device being positioned on the disc with the dispensing portion facing the waste reservoir, whereby during operation of the disc, the waste reservoir collects dispensed fluid.

In an embodiment, the microfluidic system further comprising a reaction detecting/analyzing device for detecting and/or analyzing the reaction occurring in the reaction chamber.

In accordance with yet another aspect of the present invention, there is provided a method for driving fluids used in a reaction within a microfluidic structure, the method comprising:

(a) providing a microfluidic structure comprising a microfluidic flow network interfaced with a removable-member for defining a reaction chamber therebetween, the reaction chamber being in fluid communication with the network;

(b) placing at least one sample fluid product within the network and at least one reacting product in one of the network and the reaction chamber;

(c) actuating the microfluidic flow network so that products in the network are driven to the reaction chamber for providing a reaction therein; and (d) removing at least a part of the removable-member from the network with a result of the reaction being provided on either the removable-member or the network or both.

In an embodiment, this method further comprises: (e) detecting and/or analyzing the reaction.

In an embodiment, (e) is performed before (d) so that the reaction is detected and/or analyzed within the reaction chamber. In an embodiment, the reaction is detected and/or analyzed on either the removable-member or the network or both.

In an embodiment, the at least one sample fluid product comprises a reagent. In another embodiment, the at least one sample fluid product comprises a liquid phase analyte. In an embodiment, the at least one of the sample fluid product and the reacting product is initially provided as a dry product, the method comprising liquefying this dry product prior to step (b). In an embodiment, the at least of one of the sample fluid product and the reacting product is initially provided as a dry product, the method comprising liquefying the dry product after the placing in step (b).

In an embodiment, the reacting product comprises a fluid. In another embodiment, the reacting product comprises a solid substance. In an embodiment, the reacting product comprises bioprobes.

In an embodiment, the removable member comprises a support, the network is interfaced on the support. In an embodiment, placing the at least one reacting product in said reaction chamber in step (b) comprises placing said reacting product on this support prior to interfacing said network on said support thereby defining said reaction chamber.

In an embodiment, the reaction comprises a hybridization reaction.

In an embodiment, actuating comprises subjecting the microfluidic flow network to a force selected from the group consisting of: gravity, centrifuge, capillary force, centripetal force, gas-pressure, electro-osmosis, DC and AC electrokinetics, electrophoresis, electrowetting, magnetic force, acoustic force, pneumatic drive force, mechanical micro-pump force, positive and negative displacement force, thermal force, electrochemical bubble generation force, and combinations thereof.

In an embodiment, the network comprises a series of fluid-receiving portions from a proximal to distal position relative to the reaction chamber, step (b) comprising placing a respective said sample fluid in each of the series of fluid-receiving portions, the actuating in step (c) causing fluid products in the series of the fluid-receiving portions to be sequentially driven to the reaction chamber from the most proximal positioned to the most distal positioned fluid-receiving portion. In an embodiment, the actuating in step (c) comprises centrifugation, the sequential driving of fluids being caused by a progressive augmentation of centrifugation speed.

In an embodiment, the actuating in step (c) comprises centrifugation. In an embodiment, this centrifugation step comprises:

placing the interfaced network and removable-member on a rotatable platform; and actuating the platform so as to apply centrifugal force on the fluid products in the network.

In an embodiment, step (c) further comprises dispensing fluid-waste from the microfluidic structure via a dispensing portion thereof.

In an embodiment, the method further comprises collecting fluid waste during centrifugation via a fluid-waste-collecting portion formed on the rotatable platform.

A particular embodiment of the present invention relates to a microfluidic device that enables to drive liquid phase analytes, molecules or other solutions over microarrays of biomolecules.

The present invention relates to a removable microfluidic system. More precisely, the present invention relates to a microfluidic platform comprising a microarray of bioprobes covered by an elastomeric substrate engrafted with a microfluidic network. Fluids are moved through this network by external forces. The substrate is reversibly bound to the microarray allowing watertightness of the system. The microfluidic substrate can be removed off the microarray allowing it to be analysed externally in a commercial scanner (e.g. scanner based on confocal microscopy).

The present invention further relates to a device that increases reaction reproducibility, reaction efficiency, and which reduces reaction times and reagent volumes.

The present invention also relates to a rapid and simple removable fluidic system enabling to drive liquid phase analytes and other solutions over microarrays. In one embodiment, fluids are driven into an elastomeric material engraved with microfluidic circuitry juxtaposed above the microarray. In a preferred embodiment, the microarray is engraved on glass, plastics or any other support. In a more preferred embodiment, the elastomeric material is polymethylsiloxane (PDMS).

The present invention also relates to a microfluidic system comprising a connected waste reservoir located outside the slide support or any other support, to allow complete drying of the support prior to its analysis. The slide support may be made of glass, plastics or any other material. In a particularly preferred embodiment, the waste reservoir is a groove surrounding a disk-shaped slide support in a microfluidic system driven by centrifugal force. Each microfluidic system is preferably sealed to prevent carryover contamination by aerosols.

The present description refers to a number of documents, the content of which is herein incorporated by reference in its entirety.

Further scope and applicability will become apparent from the detailed description given hereinafter. It should be understood however, that this detailed description, while indicating preferred embodiments of the invention, is given by way of illustration only, since various changes and modifications within the spirit and scope of the invention will become apparent to those skilled in the art.

BRIEF DESCRIPTION OF THE FIGURES

Having thus generally described the invention, reference will be made to the accompanying drawings, showing by way of illustration only an illustrative embodiment thereof and in which.

Other objects, advantages and features of the present invention will become apparent upon reading of the following non-restrictive description of embodiments with reference to the accompanying drawing, which are exemplary and should not be interpreted as limiting the scope of the present invention.

DESCRIPTION OF THE EMBODIMENTS

With reference to the appended drawings, embodiments of the invention will be herein described.

Figure 1:
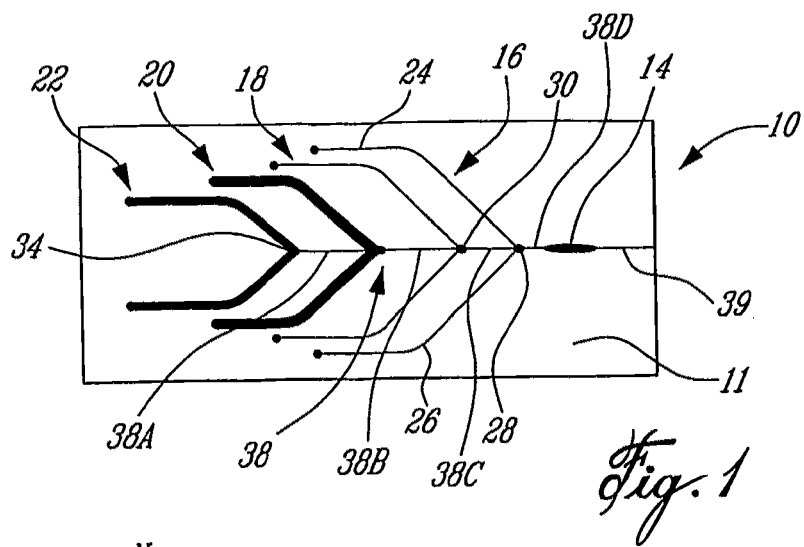
FIG. 1 is top plan view of a microfluidic flow cell in accordance with an embodiment of the present invention.
Figure 2:
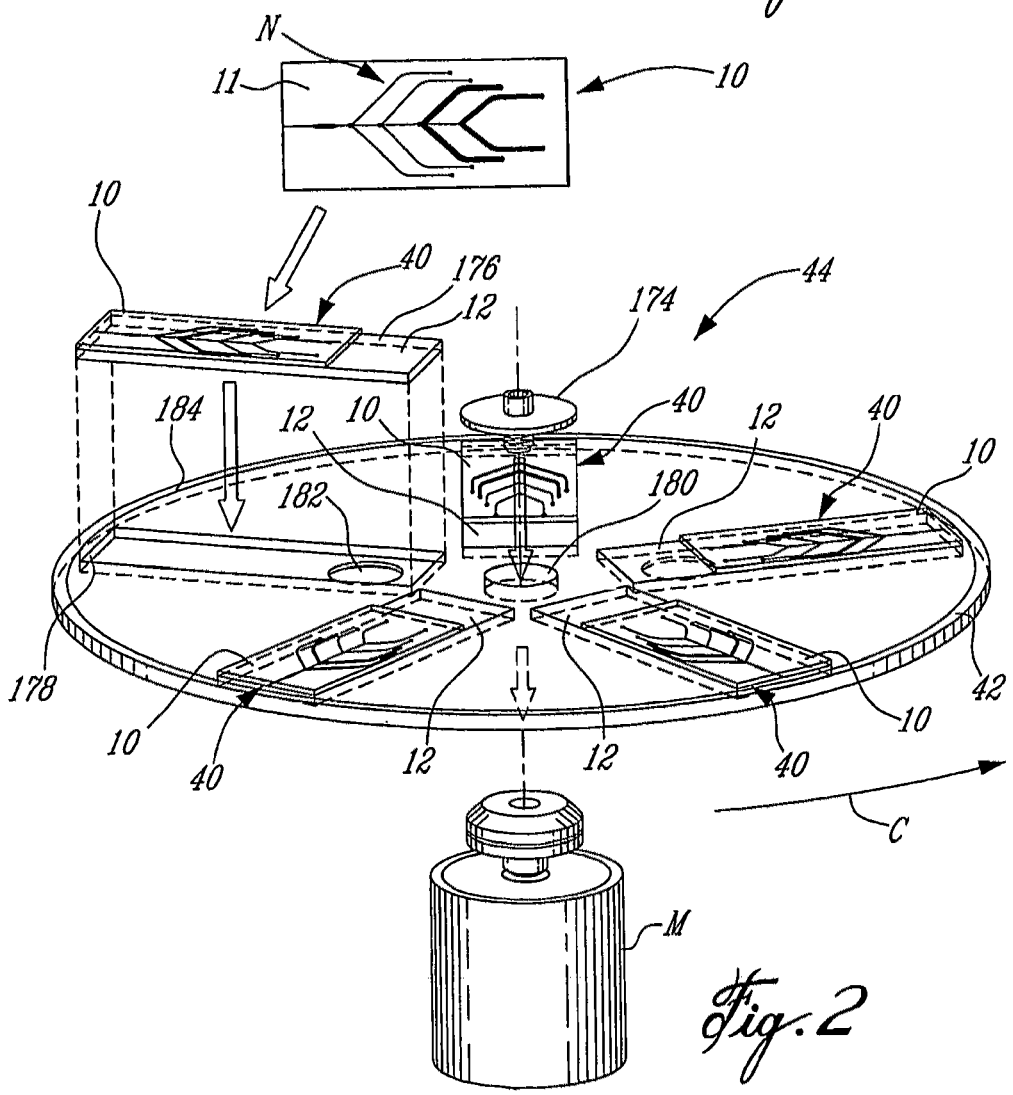
FIG. 2 is a schematic illustration of a microfluidic system in accordance with an embodiment of the present invention.

With reference to FIGS. 1 and 2, there is shown a microfluidic flow cell 10 which can be removably interfaced with a removable member 12 such as a support, which can be a slide, for example.

The microfluidic flow cell 10 comprises a reaction portion 14, which defines a reaction chamber with the support 12, as will be described herein. Furthermore, the microfluidic flow cell 10 includes fluid-receiving portions 16, 18, 20, and 22. Each fluid-receiving portion 16, 18, 20, and 22 comprises a respective fluid-receiving chamber made of two similar elongated bores 24 and 26 (only one pair of bores are referenced here) within the microfluidic cell body 11. The elongate bores 24 and 26 of each fluid-receiving chamber defined by the fluid-receiving portions 16, 18, 20, and 22 meet at a common area 28, 30, 32, and 34 respectively along a common canal 38, which is in fluid communication with the reaction chamber 14.

When the support 12 and the microfluidic flow cell 10 are in a interfaced position as shown in FIG. 2, the microfluidic cell 10 is adapted to cause fluid in the fluid-receiving portions 16, 18, 20, and 22 to flow to the reaction chamber 14.

In this non-limiting embodiment, the microfluidic flow cell 10 in combination with the support 12, defines a microfluidic device 40, which is placed on a rotatable platform or disc 42. This rotatable platform rotates as shown by arrow C thus applying centrifugal force to the microfluidic flow cell 10 comprising fluid within the fluid-receiving portions 16, 18, 20, and 22. As shown, chambers 16, 18, 20, and 22 are positioned within the body 11 of the microfluidic flow cell 10 from a proximal to a distal position relative to the reaction chamber 14. In this way, when centrifugal forces are applied upon the microfluidic flow cell 10, fluids will flow towards the reaction chamber 14 from the most proximal chamber 16 to the most distal chamber 22 as the speed of the rotational disc 42 will increase, thus increasing the centrifugal forces.

In the embodiment, shown in FIGS. 1 and 2, the microfluidic flow cell 10 is a PDMS substrate unit 11 with an engraved microfluidic network N, is applied to the support 12, in the form of a glass slide on which nucleic acid capture probes have been arrayed (not shown). The glass slide 12 with the PDMS microfluidic flow cell 10 is placed on a compact disc support 42 that can hold five slides 12 in this case, thus defining a microfluidic system 44. This microfluidic system 44 can be designed to accommodate any number of slides.

During operation, the prehybridization buffer in chamber 16 is released first and flows over the hybridization chamber 14 where the oligonucleotide capture probes are spotted onto the glass support 12. Subsequently, the sample in chamber 18 is released at a higher angular velocity. Then, the wash buffer in chamber 20 and the rinsing buffer in chamber 22 start to flow sequentially at even higher angular velocities. The wash and rinsing buffers are used to wash away the nonspecifically bound targets after the hybridization reaction.

Figure 3:
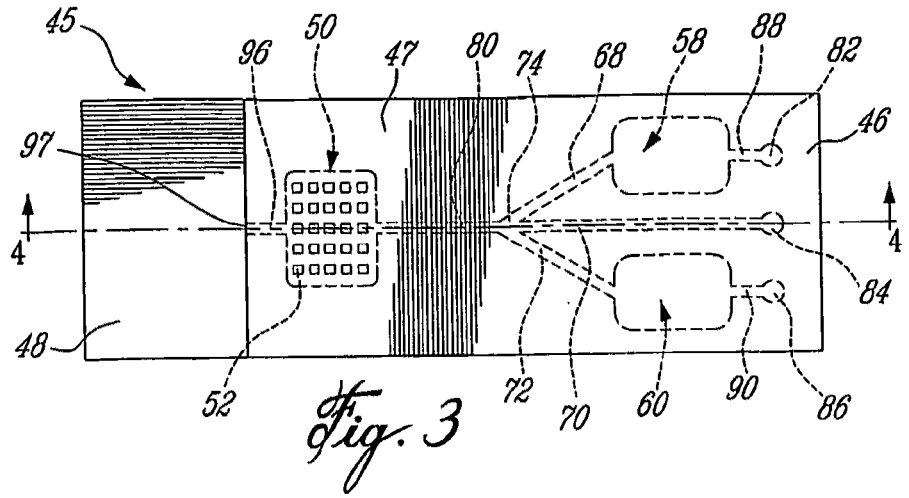
FIG. 3 is a top plan view of a microfluidic device in accordance with another embodiment of the present invention.
Figure 4:
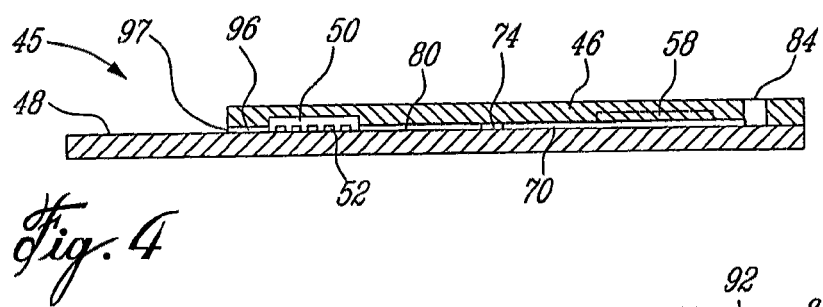
FIG. 4 is a lateral view of the microfluidic device of FIG. 3.
Figure 5:
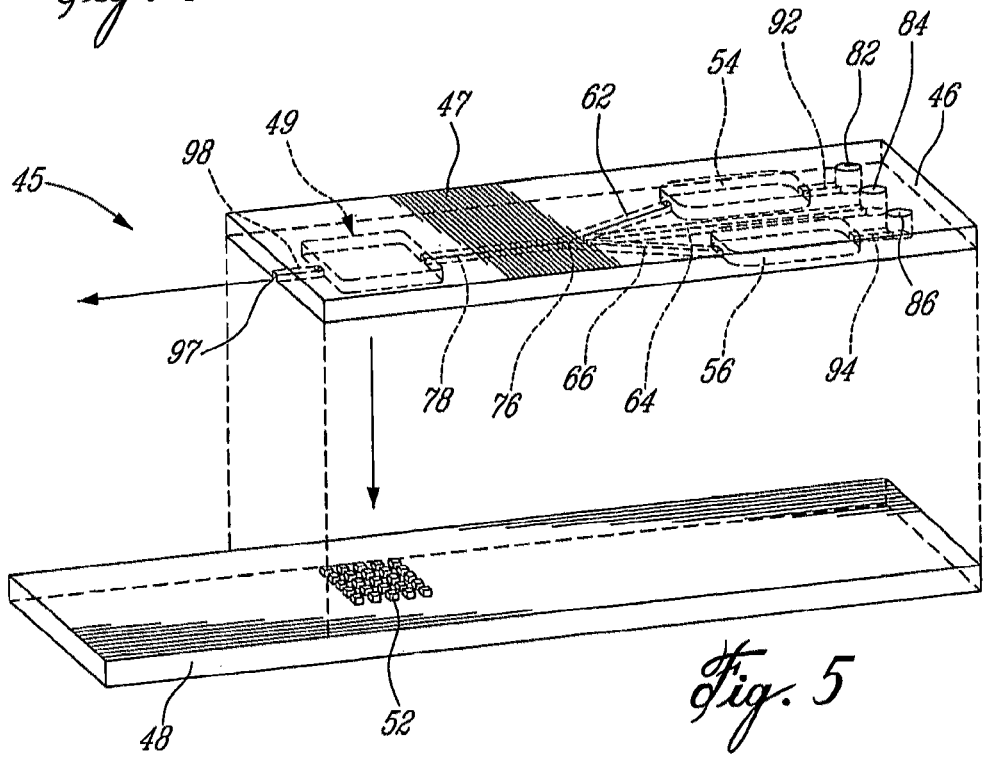
FIG. 5 is a perspective view of the microfluidic device of FIG. 3 showing the removable microfluidic flow cell and support in a separated position in accordance with an embodiment of the present invention.

With reference to FIGS. 3, 4 and 5, there is shown a microfluidic flow device 45 in accordance with another embodiment of the invention.

FIGS. 3 and 4 show the microfluidic device 45 including a removable microfluidic flow cell 46 interfaced with removable-member 48 in the form of a support. FIG. 5 shows the microfluidic flow cell 46 having been removed from support 48.

The microfluidic flow cell 46 includes a body 47 having a reaction portion 49 (see FIG. 5) in the form of a cavity. The reaction cavity 49 defines a reaction chamber 50 (see FIGS. 3 and 4) when interfaced with the support slide 48. The reaction chamber 50 provides a space for the microarray 52 on the support slide 48. Furthermore, the microfluidic flow cell 46 includes fluid-receiving portions 54 and 56 in the form of cavities as shown in FIG. 5. As shown in FIGS. 3 and 4, these fluid-receiving cavities 54 and 56 define respective fluid-receiving chambers 58 and 60 when interfaced with the slide support 48. Turning back to FIG. 5, the microfluidic flow cell 46 also includes conduit cavities 62, 64 and 66 that define respective conduits 68, 70 and 72 as shown in FIGS. 3 and 4 (when the flow cell 46 is interfaced with support 48). Conduits 68, 70 and 72 meet at a valve 74, which is defined by a valve cavity 76 (see FIG. 5) when the flow cell 46 and the support 48 are in the interfaced position. FIG. 5 shows a common channel cavity 78 in the flow cell 46 that defines, when interfaced with support 48; a common channel 80 (see FIGS. 3 and 4) in fluid communication with the reaction chamber 50 and valve 74.

Air vents 82, 84, and 86 are in fluid communication with the ambient environment. Air vents 82, 84, and 86 are respectively in fluid communication with fluid-receiving chamber 58, via conduit 88, with the valve 74, via conduit 70 and with the fluid-receiving chamber 60, via conduit 90. Turning to FIG. 5, conduits 88 and 90 are defined by conduit-cavities 92 and 94 when interfaced with support 48.

The microfluidic cell 46 also includes an evacuation duct 96 in fluid communication with the reaction chamber, providing for excess or waste fluid to flow there through into the ambient environment or on the support 48 via aperture 97. With reference to FIG. 5, duct 96 is formed by a duct cavity 98 when interfaced with support 48.

Hence, the removable microfluidic flow cell 46 and the removable solid support 48 provide a microfluidic device 45 for microarray analyses in accordance with an embodiment of the present invention.

FIGS. 6 to 10 show a variety of non-limiting embodiments of the microfluidic flow cell, removable member and microfluidic devices in accordance with the present invention.

Figure 6:
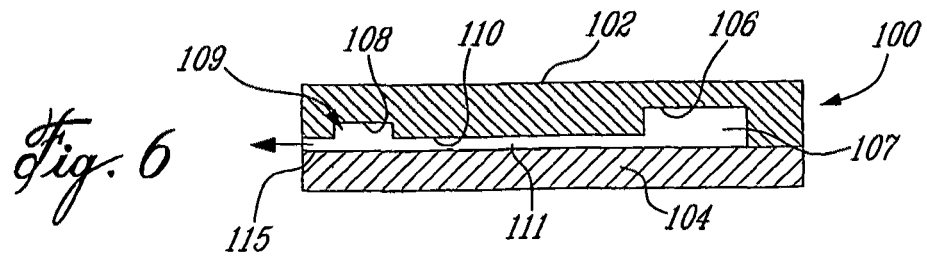
FIG. 6 is a lateral view of a microfluidic device in accordance with a further embodiment of the present invention.

FIG. 6 shows a microfluidic device 100 having a microfluidic flow cell 102 being removably interfaced with a removable member 104 in the form of a support. The microfluidic flow cell 102 has a fluid-receiving portion 106 in the form of a cavity that defines a fluid-receiving chamber 107 when interfaced with support 104. The microfluidic flow cell 102 also includes a reaction portion 106 in the form of reaction-chamber cavity 108 that defines a reaction chamber 109, for performing a reaction therein, when interfaced with the support 104. A conduit-cavity 110 defines a conduit 111 with support 104. A waste dispensing duct 115 may also be provided.

Figure 7:
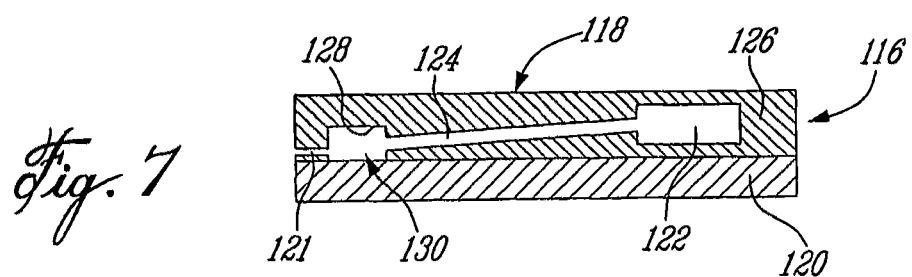
FIG. 7 is a lateral view of a microfluidic device in accordance with yet another embodiment of the present invention.

FIG. 7 shows a microfluidic device 116 having a microfluidic flow cell 118 removably interfaced with a removable member 120 such as a support. The flow cell 118 includes a fluid-receiving chamber 122 as well as a conduit 124, in fluid communication therewith, both formed within the cell body 126. The conduit 124 is in fluid communication with a reaction portion 128 in the form of cavity and defining by a reaction chamber 130 when interfaced with the support 120. A waste dispensing duct 121 may also be provided.

Figure 8:
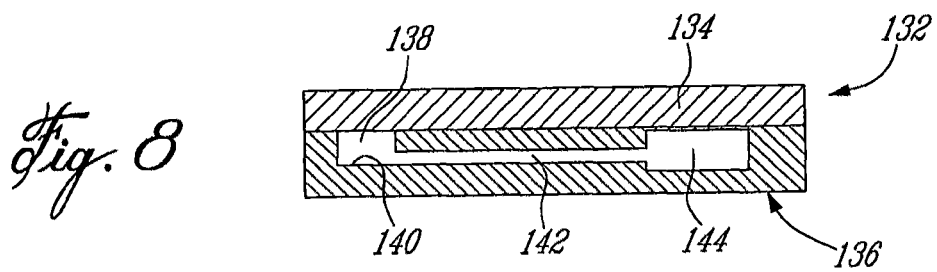
FIG. 8 is a lateral view of a microfluidic device in accordance with yet a further embodiment of the present invention.

FIG. 8 shows a microfluidic device 132 having removable member 134 in the form of a removably positioned on a microfluidic flow cell 136. The reaction chamber 138 is defined by a cavity 140, formed within the microfluidic flow cell 136 and by the enclosure member 134 when interfaced therewith. Optionally, the conduit 142 and the fluid-receiving portion 144 may be cavities enclosed by the removable member 134 or may be fully formed within the microfluidic flow cell 136.

Figure 9:
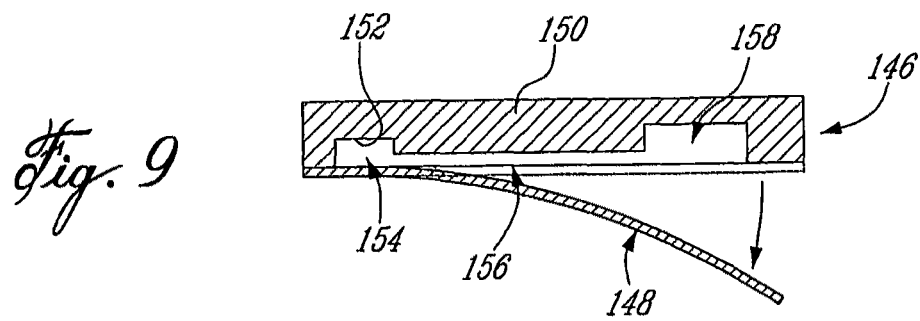
FIG. 9 is a lateral view of a microfluidic device in accordance with still another embodiment of the present invention.

FIG. 9 shows a microfluidic flow device 146 having a removable member 148 in the form of seal which, when interfaced with the microfluidic flow cell 150 at the cavity 152 thereof, defines the reaction chamber 154. Again as before, the conduit 156 and the fluid-receiving portion 158 may be cavities enclosed by the removable seal member 148 or may be fully formed within the microfluidic flow cell 150. The seal 148 may be mounted to the microfluidic flow cell 150 by a variety of adhesive materials as is known in the art.

Figure 10:
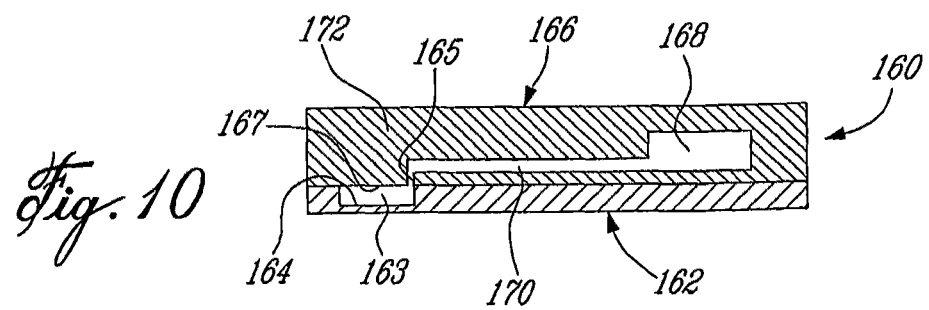
FIG. 10 is a lateral view of a microfluidic device in accordance with still a further embodiment of the present invention.

FIG. 10 shows a microfluidic flow device 160 having a support member 162 comprises a cavity 164 that defines a reaction chamber 163 when interfaced with the microfluidic flow cell 166. The microfluidic flow cell 166 includes a reaction portion 163 that comprises an exit aperture 165 in communication with a fluid-receiving portion 168 via a conduit 170 and an enclosing portion 167. Again, in this embodiment, the conduit 170 and fluid-receiving portion 168 are formed within the microfluidic flow cell body 172, yet it can be contemplated by the skilled artisan to define cavities within the microfluidic flow cell surface 172 that provides chambers when interfaced with the support 162.

In another non-illustrated embodiment, two microfluidic flow cells of the present invention can be removably interfaced with each other, as such one of the two cells acts as a removable member.

The microfluidic flow cells of the present invention are adapted to provide for fluids to flow the reaction chambers of the present invention by applying an external force onto the microfluidic flow cells such as gravity, centrifuge, capillary force, gas pressure, electro-osmosis, electrokinetics, electrowetting, magnetic pump force or any combination of the foregoing as will be understood by the skilled artisan.

In an embodiment, the present invention describes a removable microfluidic flow cells adaptable to arrays printed onto a surface or surrounded by such a surface. The different solutions required for biochemical reactions are driven onto the slide by microfluidic circuitry or network (such as N) engraved into an elastomeric substrate juxtaposed onto the surface surrounding the microarray. External forces can be applied to move the fluids; access to various parts of the circuitry or network is valve-controlled. Non-limiting examples of such external forces are pumps, magnetic, electrokinetic, electro-osmotic and centrifugal. In one embodiment, centrifugal forces can be produced by a motor or a centrifuge and move the fluids into the microfluidic channels and chambers engraved in the surface of the elastomeric substrate positioned above the microarray. The present invention comprises a microfluidic device having one or more individual chambers connected with one or several reaction chamber(s). The channels and chambers of the microfluidic system of the present invention may access individual spots or group of spots (rows, columns, blocks of spots) of the microarray or the entire microarray. Chamber and channel volumes are generally kept as small as possible to reduce the amount of sample and reagents that must be used.

In an embodiment, the devices, methods and systems of the present invention comprise microarray surfaces that are functionalized with an appropriate coating allowing for the binding of probes. The slide format can be adapted to standard microarray equipment used in proteomic or genomic laboratories.

Each chamber may contain buffers and samples necessary for the reaction(s) to proceed. Small volumes of the fluid sample comprising the biomolecules are forced to flow into the microfluidic circuitry or network positioned directly above the immobilized probes of the microarrays. The close proximity between the solution phase analytes and the bound probes speeds-up the kinetic interactions, thereby reducing reaction time.

In a particular embodiment of the present invention, a standard microscope glass-slide is chemically functionalized to covalently bind bioprobes. The microfluidic device may be used to drive fluids over spot-bearing microarrays. The bioprobes spots may be composed of DNA, RNA, oligonucleotides, oligonucleotide analogs, proteins, peptides, organic molecules, sugars, drugs or combinations thereof, or any binding partner of a substrate present in the test sample. Various reaction steps can be performed with the bound molecules of the microarray including exposure to liquid reagents or reactants, washing reagents, hybridization or detection reagents. The progress or outcome of the reaction can be monitored at each spot of the microarray in order to characterize molecules immobilized on the slide.

Presently, most custom microarrays are printed onto standard microscope glass slides; this format being required by most of the current commercially available instruments used to scan for detection signals (e.g., fluorescent signal) indicative of positive interactions with particular probes spotted on the slide. In one embodiment of the invention, the removable microfluidic platform, unit or cell was thus designed to fit standard glass slides. However, any microarray format flat surface (e.g. glass support, plastic support) can be used in accordance with the present invention. Furthermore, such a system may be used in concomitance with independent or integrated microfluidic systems for test sample preparation (e.g. for nucleic acid extraction) and/or target amplification (e.g. nucleic acid amplification by polymerase chain reaction) for molecular diagnostics. Such a system may also be a micro total analysis system.

The present invention provides microfluidic flow cells that can be adapted to interface with glass microscope slides and similar planar surfaces. This microfluidic interface system enables the delivery of sample, interacting reagents (e.g., hybridization solutions, binding solutions and the like), wash solutions, and detection reagents to selected positions on the array.

In an embodiment, grooves or indentations on the surface of the microfluidic flow cells of the invention are aligned with spots on the microarray, so that when the microfluidic interface system is sealed onto the microarray surface, the indention and grooves form channel(s), reagent reservoir(s) and/or reaction chamber(s) containing the spots of the microarray(s).

In one particular embodiment, a soft elastomeric material (e.g., PDMS) is selected to make the microchambers and channels of the microfluidic interface system. PDMS-based elastomers are low cost materials which can be molded and which seal reversibly with flat and smooth surfaces such as glass.

In a further particular embodiment, centrifugal forces are used to move the fluids into the microfluidic channels and chambers positioned above the microarray.

In yet a further particular embodiment, a standard microscope glass slide support is designed to fit into a centrifugation system. The centrifugation system may be a custom device or a classical bench centrifuge. The centrifugation system comprises a step by step motor, controlled by a computer.

The controlled delivery of fluids to one or more selected regions of the microarray slide may be accomplished by choosing the appropriate size and shape of the channels and chambers of the microfluidic system, and by selecting the optimal centrifugal force and the optimal time over which the centrifugal force will be applied to deliver the fluids over the microarrays.

In yet a further particular embodiment of the present invention, the microfluidic system is used for the analysis of nucleic acids including but not limited to molecular diagnostic assays on microarrays for infectious disease agents which typically require rapid, sensitive, automated, high throughput and inexpensive systems.

As mentioned herein above, the slide can be made of glass, glass being the most commonly used support material for custom microarrays of nucleic acids and proteins. The glass slide is specifically coated to optimize the binding of nucleic acids or nucleic acid analogs (e.g. peptide nucleic acid, locked nucleic acid). Microarrays of nucleic acid probes are printed onto the glass slides using an arrayer positioned to fit directly under the hybridization chambers of the invention when the microfluidic circuitry or network (such as N shown in FIG. 2) engraved elastomeric material is placed above the slide supports of the invention. Microarrays may include numerous different probes and can be used to perform expression profile experiments. The corresponding hybridization chamber(s) can therefore be designed to accommodate the required volumes, in order to be used as an automated hybridization platform. In a particular embodiment, the array is linear and made-up of spotted probes, and is fitted to be used for diagnostic purposes. The hybridization chamber(s) can also be designed to accommodate smaller volumes allowing flow-through hybridization, thus enhancing the hybridization kinetics. This reduces the hybridization time and/or increases the sensitivity of the reactions required for detection of hybrids.

In comparison with passive hybridization, the microfluidic device of the present invention allows for about 6-fold increase in the hybridization kinetics as demonstrated for a 20-mer oligonucleotide as well as for a 368-bp amplicon (see Example 1). Furthermore, it was possible to detect and discriminate 4 clinically relevant *Staphylococcus* species using a 15-minute hybridization process. This is at least 16 times faster than the times generally required for passive hybridization. The removable microfluidic system of the present invention allows to automate and speed up reaction processes using conventional microarrays and provides for the rapid detection and identification of nucleic acids or other biomolecules present in a sample (proteins, cofactors, drugs and the like). The removable microfluidic flow cells as well as microfluidic devices of the present invention can be used in a variety of applications such as in the biomedical field (detection of the presence of pathogens or disease associated markers), in the forensic field (identification of individuals), in basic research as well as in other industrial applications. Finally, the removable microfluidic flow cells and devices of the present invention can be applied in any type of microarray analysis.

In one non-limiting embodiment, the substrate comprising the body of the microfluidic flow cell of the present invention is a soft elastomeric material capable of reversibly binding to the microarray by Van der Waals forces without the need for any glue or clamp. In a particularly preferred embodiment, the soft substrate is made of PDMS. The microfluidic circuitry of network is engraved into the substrate using classical microfabrication technologies such as photolithography and computer numerically controlled (CNC) machining. Various types of valves may be included in the microfluidic circuitry or network. Valves are designed to control the release of fluids from the different reservoirs. For example, the valves can be electromagnetically actuated microvalves (Canapu et al., 2000, J. Microelectromech. Syst., 9:181-189), air driven pressure valves (e.g., to control the venting of air in specific regions of the microfluidic circuitry, therefore modulating the backpressure that opposes fluid movements) (Unger et al., 2000, Science, 288:113), hydrogel valves (Liu et al., 2002, J. MEMS, 11:45-53), and centrifugal valve (Madou et al., 2001, Sensor Actuat. A, 91:301-306). Alternatively, movements of fluids in the microfluidic system may be driven without the use of valves. For example, fluids can be moved by sequential flow of different liquids separated by air bubbles or other non-mixing boundary.

Turning back to FIGS. 1 and 2, a microfluidic system 44 is illustrated. The microfluidic flow cell 10 comprises a circuitry or network N engraved into a PDMS substrate 11. The PDMS substrate 11 is aligned and reversely bound to a microarray (not shown) printed onto a glass slide 12 by applying pressure to form a functional microfluidic device 40. After printing the oligonucleotide microarray onto the glass slide 12 using a commercial arrayer, the PDMS microfluidic circuit N is superposed onto the glass slide 12 in such a way that the PDMS engraved hybridization chamber 14 is above the microarray. The microfluidic device 40 (glass slide 12 and PDMS 11) was introduced into a custom-made plastic disc shape support 42 comprising an opening and fixed on the actuator hub 174 of a motor M. The disc 42 is rotated, as shown by arrow C, to drive sample and buffers directly onto the glass surface 176 using centrifugal forces to move the liquid reagent into the chamber 14 and microfluidic channels 30 (Madou et al., 2001, Sensor Actuat. A, 91:301-306). At the end of the process, the PDMS fluidic circuits N were pealed off the glass slide 12 and the microarray was analysed using commercial instruments. This system 44 allows for dynamic DNA hybridization (flow-through) generated by centrifugal forces. In the present invention, such a microfluidic system was able to discriminate nucleic acid sequences including single nucleotide polymorphisms (SNPs) in a fraction of time required by conventional microarray technology.

If centrifugal forces are used to drive the fluids in the microfluidic chambers and channels, the valves (such as 38, 30, 32 and 34) can be designed to burst at different rotational speeds (FIG. 1). The circuitry or network N may comprise a hybridization chamber 14, a pre-hybridization buffer reservoir 16, a sample inlet 18, a washing reservoir 20, and a rinsing reservoir 22, all connected together by different sized channels 38A, 38B, 38C, 38D and 38E (FIGS. 1 and 2). The chamber 14 is in fluid communication with a dispensing portion 39 in communication with the ambient environment. The different buffers and the sample are forced to flow-through the hybridization chamber 14 positioned above the microarray on support 12, by varying the rotation speed of the centrifugal system 42. The architecture of the hybridization chamber 14 may be adapted to enhance the turbidity of the fluid, thus enhancing the hybridization kinetics. Again, movements of fluids in the microfluidic system may alternatively be driven without the use of valves as described above.

The methods, systems and devices of the present invention use a microarray support to connect the microfluidic system to the device providing the force to move the fluids. The force can be generated by pneumatic drive, mechanical micropumps, electro-osmosis, electrophoresis, gas-pressure, positive and negative displacement, thermal, electrochemical bubble generation, acoustics, magnetic, DC and AC electrokinetics, and centripetal forces. In a particular embodiment, the support is a disc 42 adaptable to a rotational device 174 providing the centrifugal forces to move the fluids. In a more particular embodiment the support is a disc 42 comprising microfluidic device receiving portions 178 such as slots accommodating standard microscope slides 12. Each slot 178 is placed at the same distance from the disc center 180, allowing for equal centrifugal forces to be applied to each slotted slide. The disc is designed to be fixed on the hub 174 of a motor M. Each slide 12 may comprise an aperture 182, to facilitate removal of the slides 12 after centrifugation. In a related embodiment, a waste reservoir 184 such as a furrow is engraved into the support disc 42 to collect the hybridization waste liquid following centrifugation, allowing the slides 12 to dry completely. In a another related embodiment, the microfluidic system 44 comprising disc 42 is sealed (not shown) to avoid aerosols generation during the spinning of the disc 42.

The force-providing devices of the present invention can be any device, such as a pump, a heater, a motor, a magnetic device, a mechanical device, or an electrical device. The device providing the centrifugal forces to force the fluids to the microarray support is preferably a motor. The motor may be a step by step motor, or a computer-driven or a programmable, commercially available bench centrifuge.

Although the microfluidic flow cells (10, 46) of the present invention have been designed, in a particular embodiment, to interface with slides (12, 48) bearing microarrays (such as 52) of biomolecules, they may also be used to provide a fluid interfacing with a support bearing various types of molecular probes or samples. The probes or samples could be on bead or particles located on the support. It is to be understood that the application of the present invention is not to be limited to the use with microarray slides. This invention could be applied to detect/analyse any reaction signals which may be optical, electrical, mechanical, chemical, magnetic or any other measurable property of said reaction.

The present invention is illustrated in further detail by the following non-limiting examples.

EXAMPLES

Example 1

Removable Fluidic System to Drive Microarray Reagents Using Centrifugal Force

Materials and Methods

Selection of PCR Primers and Capture Probes

All chemical reagents were obtained from Sigma-Aldrich Co. (St-Louis, Mich.) and were used without further purification unless otherwise noted. Oligodeoxyribonucleotide capture probes, which were 5'-modified by the addition of two nine carbon spacers and an amino-linker, were synthesized by Biosearch Technologies (Novato, Calif.). The amino-linker modification permits the covalent attachment of probes onto a functionalized glass surface. Four capture probes were used: *S. aureus* targeting probe (5'-CGTATTATCAAAAGACGAAG-3'), *S. epidermidis* targeting probe (5'-CAIAGCTGAAGTATACGTAT-3'), *S. haemolyticus* targeting probe (5'-CAAAATTTAAAGCAGACGTATA-3') and *S. saprophyticus* targeting probe (5'-AAAGCGGATGTTTACGTTTT-3'). Primer pairs TstaG422 (5'-AAAGCGGATGTTTACGTTTT-3') and TstaG765 (5'-TIACCATTTCAGTACCTTCTGGTAA-3') were used to amplify all *staphylococcal* species. Used genomic DNAs were purified from strains *S. aureus* ATCC 43300, *S. epidermidis* ATCC 14990, *S. haemolyticus* ATCC 29970 and *S. saprophyticus* ATCC 35552.

Fabrication of the Elastomeric Flow Cell

The microfluidic structures were fabricated using PDMS replicating techniques (Duffy et al., 1998, Anal. Chem., 70:4974-4984). A novel 2-level SU-8 process was developed in order to achieve the desired 2-level PDMS fluidic structures that provide sufficient volume for reagent storage while also enabling the proper flow rate for reagent manipulation and for hybridization in the shallow hybridization chamber.

SU-8 Mold Fabrication

SU-8 is a negative tone photoresist that has attracted significant interest for the fabrication, as well as for applications requiring very thick photoresist layers. Due to its excellent UV transparency, standard UV lithography can be used to craft LIGA-like MEMS devices. SU-8 photoresists come in different viscosities: the lower viscosity products are more suited for the fabrication of thin structures (up to 2 µm); the more viscous SU-8 photoresists are better suited for thick layers (mm scale). Two types of the photoresist, SU-8 25 and SU-8 100, available from Microchem Inc. (Newton, Mass.), were used. SU-8 25 was used for the microchannel structures and SU-8 100 was used for the much larger reagent chambers. In the first step, SU-8 25 was processed on a 15 cm silicon (Si) wafer (Addison Engineering, San Jose, Calif.) to obtain the structures for the microchannels (25 µm in depth) and the alignment marks for the second SU-8 layer. Subsequently, a thick layer (250 µm) of SU-8 100 was spin-coated over the substrate on which the molds for the microchannels had been created. This thicker layer was used to define the mold for the much larger reagent reservoirs. Since crosslinked SU-8 photoresists have lower optical transparency than their unexposed surroundings, the alignment marks can be readily observed even when they are completely covered with a thick layer of the unexposed photoresist. In the pattern design, compensations were made for possible alignment errors between the two layers of photoresist. The channels and chambers overlapped in the connection areas to avoid possible disconnections caused by misalignment. Six identical molds were simultaneously fabricated onto the 15 cm Si wafer for faster replication.

Polymerization Molding of the Flow Cell

PDMS was purchased from Dow Corning (Midland, Mich.). The base (Sylguard 184 silicone elastomer) and the curing agent (silicone resin solution) were thoroughly mixed in a weight proportion of 10:1. Low temperature curing (e.g. 65° C.) in a convection oven was preferred over high temperature baking due to the thickness of the structures. High temperatures (e.g. 150° C.) causes significant thermal stress at the interface between the SU-8 patterns and the Si substrate which can actually crack the substrate and peel off the SU-8 structures. Leveling of the PDMS on the substrate is required in order to achieve a uniform thickness over all the flow cells. The appropriate combination of the macrostructures of the chambers and microstructures of the channels is important for the performance of the flow cells.

Preparation of Glass Slides

All chemical reactions were carried out in polypropylene jars at room temperature unless specified otherwise. The microscope glass slides used (VWR Scientific, West Chester, Pa.) had a surface of 25 mm×75 mm. After sonication in deionized water for 1 hour, the slides were sonicated in 40 ml of NaOH (10%) for 1 hour, washed several times with deionized water and dried under a stream of nitrogen. The slides were then sonicated in an aminopropyltrimethoxysilane solution (2 ml water, 38 ml MeOH and 2 ml aminopropyltrimethoxysilane) for 1 hour, washed with methanol, dried and baked at 110° C. for 15 minutes. The amine modified slides were activated by overnight sonication in 1,4-dioxane (40 mL) containing 0.32 g (2 mmol) of carbonyldiimidazole as the coupling agent, followed by washing with dioxane and diethyl ether, and drying under a stream of nitrogen.

Microarray Production

The probes were diluted two-fold by the addition of Array-it Microspotting Solution Plus™ (Telechem International, Sunnyvale, Calif.), to a final concentration of 5 μM. The capture probes were spotted in triplicate, using a VIRTEK SDDC-2™ arrayer (Bio-Rad Laboratories, Hercules, Calif.) with SMP3 pins (Telechem International). Upon spotting, each spot had a volume of 0.6 nL and a diameter ranging between 140 to 150 μm. After spotting, the slides were dried overnight, washed by immersion in boiling 0.1% Igepal CA-630 for 5 minutes, rinsed in ultra-pure water for 2 minutes, and dried by centrifugation under vacuum for 5 minutes (SpeedVac™ plus; Thermo Savant, Milford, Mass.). The slides were subsequently stored at room-temperature in a dry, oxygen-free environment.

PCR Amplification and Amplicon Labeling

Universal PCR primers targeting conserved areas of the tuf gene were used to amplify a 368-bp fragment from S. aureus, S. epidermidis, S. haemolyticus and S. saprophyticus purified genomic DNAs. Fluorescent dyes were incorporated during asymmetrical PCR amplification. Cy-5 dCTP (Amersham Biosciences, Baie d'Urfé, Québec, Canada) was mixed at concentrations of 0.02 μM in a 50 μl PCR mixture containing: 0.05 mM dATP, 0.02 mM dCTP, 0.05 mM dGTP, 0.05 mM dTTP, 5 mM KCl, 1 mM Tris-HCl (pH 9), 0.01% Triton X-100, 2.5 mM MgCl2, 0.5 Unit of Taq DNA polymerase (Promega, Madison, Wis.), 0.2 μM of primerTstaG765, 0.005 μM of primer TstagG422 and 1 ng of purified staphylococcal genomic DNA. Thermal cycling for PCR amplification (180 seconds at 94° C. followed by 40 cycles of 5 seconds at 95° C., 30 seconds at 55° C., and 30 seconds at 72° C.) was carried out on a PTC-200 DNA Engine Thermocycler™ (MJ Research, Reno, Nev.).

DNA Microarray Hybridization and Data Acquisition

PCR amplicons labeled with Cy5-dCTP were denatured at 95° C. for 5 minutes. Denatured labeled amplicons (5 μl) were mixed with hybridization buffer (15 μl) (8×SSPE, 0.04% PVP and 40% formamide).

Passive hybridization was performed in a 20 μl Hybri-well™ self-sticking hybridization chambers (15 mm×13 mm) (Sigma-Aldrich). Hybridization buffer containing the labeled sample was introduced in the chambers and hybridization was conducted for 5 minutes at room temperature. After hybridization, the microarrays were washed at room temperature (5 minutes) with 2×SSPE containing 0.1% SDS and rinsed once (5 minutes) with 2×SSPE at room temperature. The microarrays were dried by centrifugation at 1348×g for 3 minutes.

Flow-through hybridization was performed in the flow-cell as described above for passive hybridization. A hybridization unit consisting of a glass slide and flow-cell was placed onto a home made plastic disc support, and the support fixed to the hub of a step by step motor controlled by a computer. The labeled sample was prepared the same way as for a passive hybridization. Sample (2 μl) and washing and rinsing buffer (10 μl) were loaded onto the microfluidic unit just before spinning the disc. The disc was spun at different speeds in order to sequentially burst the centrifugal valves and allow the pre-hybridization buffer, sample, washing and rinsing buffer to flow-through a 140 nl hybridization chamber respectively. The disc was subsequently spun at 1000 rotation per minute (rpm) for 1 minute to dry the slide.

Slides were scanned using a ScanArray 4000XL™ (Packard Bioscience Biochip Technologies; Billerica, Mass.) and fluorescent signals were analyzed using its QuantArray™ software.

Results

Assembly of the Microfluidic Unit

The assembled microfluidic unit is shown in FIGS. 1 and 2. The flow cell is aligned with, and adhered to, the glass slide to form a DNA hybridization detection unit, up to 5 of which can be mounted onto the disc platform (FIG. 2). The design of the microfluidic network and the microarray layout is such that a hybridization chamber is positioned right above the oligonucleotide capture probes spotted onto the glass slide when the two parts are put together. The reagents are positioned to be sequentially pumped through the hybridization chamber by centrifugal force beginning with chamber 16. This flow sequence is achieved by optimizing the balance between the capillary force and centrifugal pressure (Madou et al., 2001, Sensor Actuat. A, 91:301-306). The pre-hybridization buffer (chamber 16) is released first and flows over the 140 nl hybridization chamber (chamber 14) where the oligonucleotide capture probes are spotted onto the glass support. The sample containing the labeled PCR amplicons (chamber 18) is then released at higher angular velocity and flows over reaction chamber 14. Then, the wash buffer (chamber 20) and the rinsing buffer (chamber 22) flow sequentially at even higher angular velocities. The wash and the rinsing buffers are used to remove the nonspecifically bound targets following the hybridization process. Pre-hybridization buffer, sample, washing buffer and rinsing buffer were collected in a waste reservoir which is a groove surrounding the disc. This system was enclosed in a box during spinning of the disc to avoid the spread of aerosols carrying PCR amplicons.

Flow-Through Versus Passive Hybridization

Figure 11:
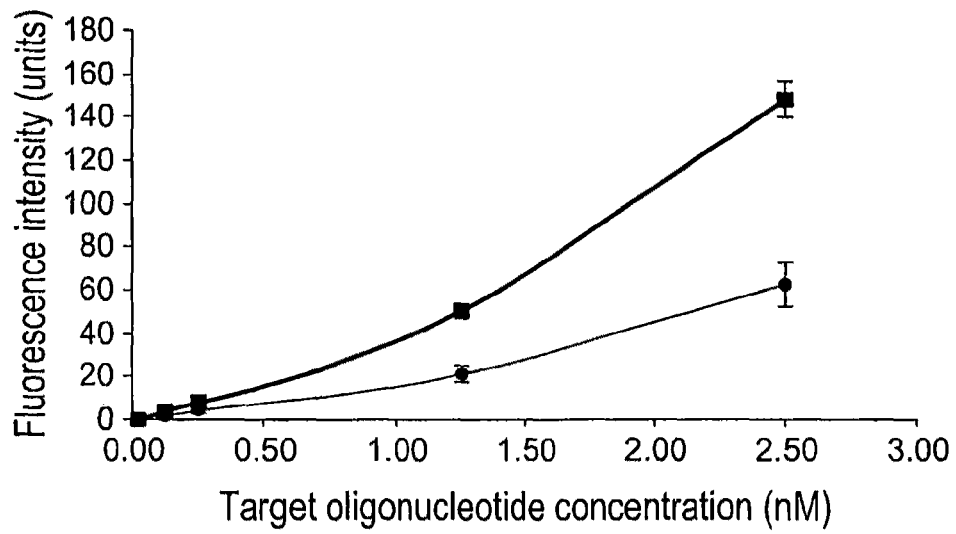
FIG. 11 illustrates a comparison between the sensitivity of labeled oligonucleotide detection in no-flow hybridization (circles) vs flow-through hybridization (squares) using a complementary 15-mer capture probe.
Figure 12:
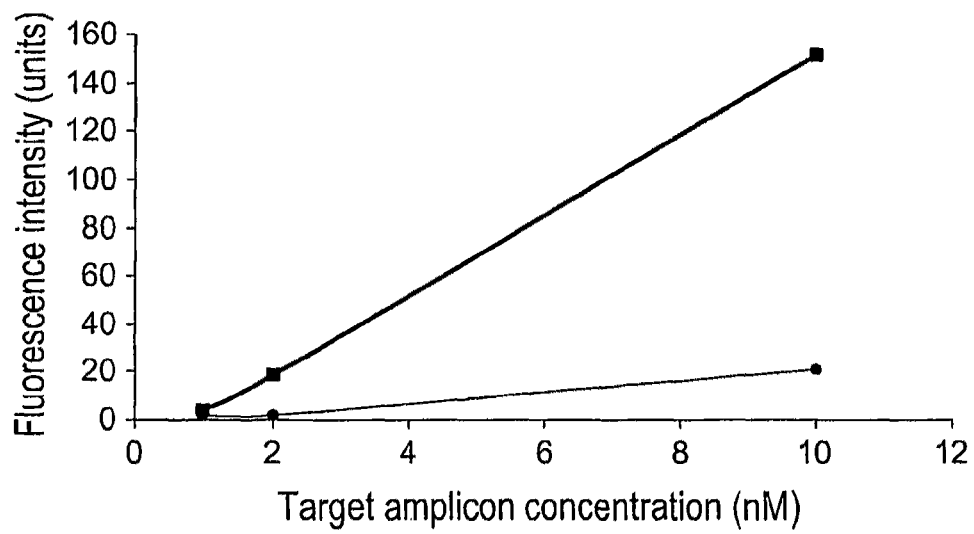
FIG. 12 illustrates a comparison between the sensitivity of labeled amplicon detection in no flow hybridization (circles) versus flow-through hybridization (squares); the amplicons (368 bp) were generated using a pair of PCR primers targeting *Staphylococcus aureus* tuf sequences; the *S. aureus*-specific capture probe was a 20-mer fully complementary to internal sequences of the 368-bp amplicon.

Cy3-labeled 20-mer oligonucleotides were hybridized both in a passive way using a standard commercially available hybridization chamber of 20 μl, and with the flow-through method using the microfluidic platform in a 140 nl of hybridization chamber as described hereinabove. For passive hybridization, 20 μl of different concentrations (i.e. 0.025, 0.125, 0.25, 1.25 and 2.5 nM) of Cy3-labeled oligonucleotides were hybridized to their complementary probes, spotted onto a microarray on glass support using Hybri-well™ self-sticking hybridization chambers (Sigma-Aldrich). Following hybridization at room temperature for 5 minutes, the slides were washed and rinsed as described above in the method section. For flow-through hybridization, 2 μl of different concentrations (i.e. 0.025, 0.125, 0.25, 1.25 and 2.5 nM) of Cy3-labeled oligonucleotide were hybridized to their complementary probes as described for the passive method. Samples of the different concentrations of oligonucleotides (2 μl) were loaded into the sample inlet of the microfluidic unit. Prehybridization buffer, sample, washing buffer and rinsing buffer were loaded respectively into chambers 16, 18, 20 and 22 of the hybridization unit shown in FIGS. 1 and 2. Loading of the reagents was performed immediately before spinning the disc platform to avoid reagent evaporation. A rotation speed of 300 rpm was selected to release the content of the pre-hybridization chamber 16 and obtain a sample flow rate of about 400 nl/min in the hybridization chamber (i.e. reaction chamber), which corresponds to a hybridization time of 5 minutes (identical to the hybridization time used in the passive hybridization experiments). Subsequently, the sample chamber (chamber 18) was released into the reaction chamber by rotating the disc at 412 rpm to achieve a flow rate of 400 nl/min. Following the hybridization step, the rotation speed of the platform was further increased to 585 and 764 rpm in order to sequentially burst the centrifugation valves, thereby releasing respectively into the hybridization chamber 10 μl of washing buffer and 10 μl of rinsing buffer, both of which flowed through the hybridization chamber with an average flow rate of 2 μl/min resulting in a total time of about 15 minutes for the entire hybridization process, including a 30 seconds drying step (high rotation speed). The PDMS microfluidic flow cells were pealed off. Following passive or flow-through hybridization, the microarrays were scanned. The fluorescence intensity was spotted against concentration of oligonucleotide (FIG. 11). It was observed that flow-through hybridization in a 140 nl chamber was more sensitive than passive hybridization in a larger volume chamber (i.e. 20 μl). The passive and flow-through hybridizations were also performed using a 368-bp Cy-labeled amplicon that is derived from tuf gene sequences. The results of these experiments show that flow-through hybridization is more sensitive than passive hybridization as observed with a complementary oligonucleotide (FIGS. 11 and 12).

Analytical Sensitivity of the Microfluidic Platform

In all the experiments described above, the standard procedure was to perform PCR amplification using universal primers targeting conserved areas of the tuf gene to amplify a 368-bp fragment from *S. aureus, S. epidermidis, S. haemolyticus* and *S. saprophyticus* purified genomic DNAs. One ng of genomic DNA purified from different strains of staphylococci was used for each PCR reaction. Approximately, 20% of the amplified PCR reaction mixture was used for each hybridization. To evaluate the minimal quantity of bacterial genome required to have a clear and unambiguous signal using the microfluidic platform, hybridization of PCR amplicons amplified from the equivalent of 10, 100, 1000 or 10000 genome copies was performed. It was found that the equivalent of as little as 100 genome copies of starting material was enough to discriminate each of the four different *staphylococcal* amplicons.

Figure 13:
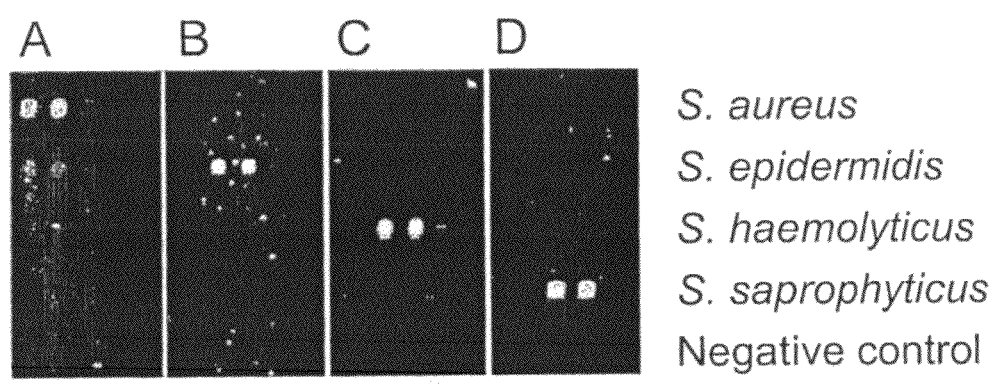
FIG. 13 illustrates flow-through hybridization of Cy-labelled tuf gene amplicons. These amplicons were labelled by PCR amplification of genomic DNA purified from four staphylococcal species and hybridization was performed by using a microarray of capture probes targeting these four staphylococcal amplicons; panels: A) Hybridization to the *S. aureus* amplicons; B) Hybridization to the *S. epidermidis* amplicons; C) Hybridization to the *S. haemolyticus* amplicons; and D) Hybridization to the *S. saprophyticus* amplicons.
Figure 14A:
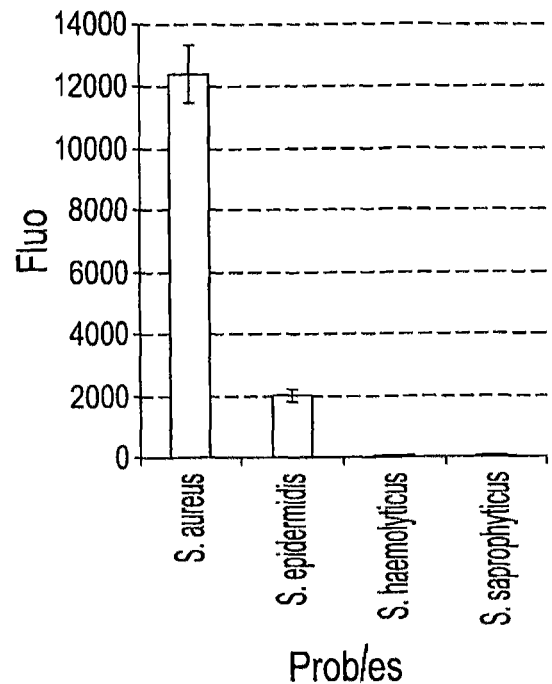
FIGS. 14A to 14D illustrate flow-through hybridization of Cy-labelled tuf gene amplicons. These amplicons were labelled by PCR amplification of 1 ng of genomic DNA purified from four staphylococcal species and hybridization was performed by using a microarray of capture probes targeting these four *staphylococcal* species. Panels are as follows: 14A) Hybridization to the *S. aureus* amplicons; 14B) Hybridization to the *S. epidermidis* amplicons; 14C) Hybridization to the *S. haemolyticus* amplicons; and 14D) Hybridization to the *S. saprophyticus* amplicons. The graphs show the fluorescence intensity for each hybridizations. Standard deviations are for the results of five hybridizations.
Figure 14B:
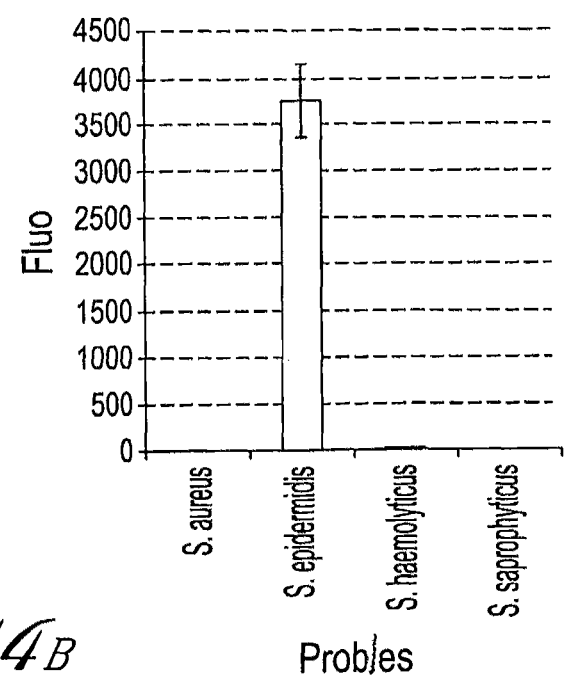
Figure 14C:
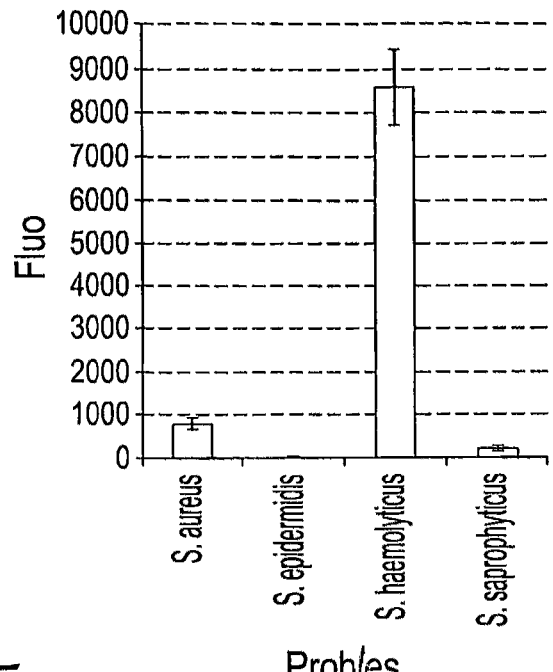
Figure 14D:
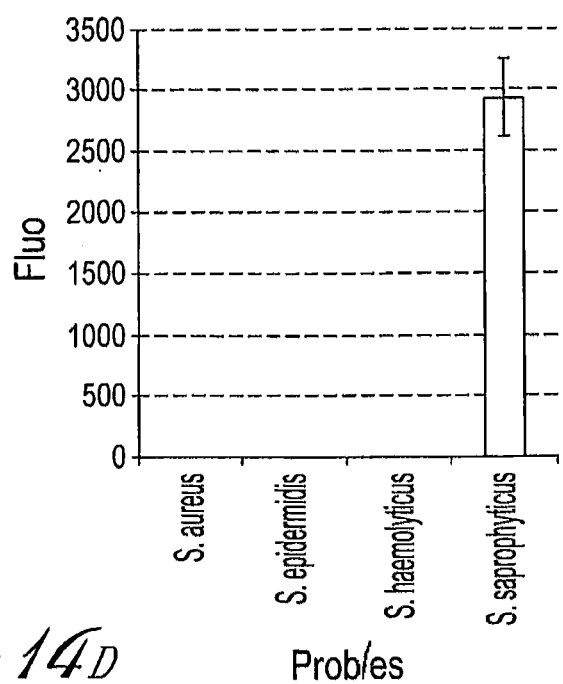

Detection and Specific Identification of Four Clinically Important *Staphylococcal* Species Microarrays of species-specific capture probes targeting each of the four *staphylococcal* species (i.e. *S. aureus, S. epidermidis, S. haemolyticus* and *S. saprophyticus*) printed in duplicate were prepared. The microarrays were then hybridized with the different staphylococcal amplicons generated by PCR amplification of genomic DNA purified from each of these four *staphylococcal* species. The results demonstrate that it was possible to detect and discriminate the four different *staphylococcal* tuf amplicons without any ambiguity (FIGS. 13 and 14). It is worth noting that there is a difference of only a single nucleotide polymorphism (SNP) between the *S. epidermidis*-specific probe and the *S. aureus*-amplicon sequence, showing that this system is able to distinguish a SNP after only 5 minutes of hybridization.

Discussion

In the genomic field, microarrays have become the standard for profiling gene expression. Thousands of genes are routinely studied for their expression using the microarray technology. Several groups have attempted to adapt this technology to the rapid detection of microbial targets for diagnostic purposes (Mikhailovich et al., 2001, J. Clin. Microbiol., 39:2531-2540; Westin et al., 2001, J. Clin. Microbiol., 39:1097-1104; Wang et al. 2003, Anal. Chem., 75:1130-1140; Bavykin et al. 2001, Appl. Environ. Microbiol., 67:922-928; Bekal et al., 2003, J. Clin. Microbiol., 41:2113-2125). Even though such systems most often require highly advanced biochips, the detection performance lacks both sensitivity and specificity (Lenigk et al., 2002, Anal. Biochem., 311:40-49; Wang et al., 2003, Anal. Chem., 75:1130-1140). As demonstrated hereinabove, very small amounts of liquid can be precisely and directly moved onto a glass slide surface from buffer chamber(s) to hybridization chamber(s) using a microfluidic elastomeric flow-cell juxtaposed above the slide. This technology allows to dramatically reduce the volumes of reagents required during microarray hybridization. For identical concentrations of a 20-mer oligonucleotide or 368-bp amplicon, the flow-though hybridization method gave signals which were of an order of magnitude higher than those obtain with passive hybridization (FIGS. 11 and 12). Theses results confirm previous observations, obtained with a more complex microfluidic device (Wang et al., 2003, Anal. Chem., 75:1130-1140). The capture probes and buffer compositions were designed in order to achieve efficient hybridization at room temperature, thereby reducing the complexity of the device.

The system of the present invention is specific enough to discriminate SNP at room temperature using a hybridization period of less than 10 minutes. The results of the discrimination specificity for four *staphylococcal* species (hybridization period of 5 minutes) are shown in FIGS. 13 and 14. Other probes have at least 3 distinct nucleotides as compared with others *staphylococcal* amplicons. In addition to being specific, the present system is also sensitive. It is possible to generate a specific hybridization signal using the amplified PCR reaction mixture containing the equivalent of as little as 100 copies of *staphylococcal* genome as starting material. This result is at least 10 times more sensitive than those obtained by other groups using more complex microfluidic devices (Westin et al., 2001, J. Clin. Microbiol., 39:1097-1104). It is worth noting that the PCR products are not purified prior to their addition to the hybridization buffer.

Overall, the present example describes an affordable, easy to use, automated and rapid custom microarray hybridization microfluidic platform. This microfluidic platform uses standard glass slides totally compatible with commercial arrayers and scanners. In this system the classical hybridization chamber or coverslip is replaced by a low cost elastomeric material engrafted with a microfluidic network. This elastomeric material sticks reversibly to the glass slide without any glue or chemical reaction thereby forming the microfluidic unit. Placed in a plastic compact disc like support, the microfluidic units are spun at different speeds to allow fluids to move. Using the present system, it was demonstrated that it is possible to detect and discriminate tuf sequence polymorphisms including SNP present in four different *staphylococcal* species using a rapid hybridization protocol of approximately 15 minutes.

It is to be understood that the invention is not limited in its application to the details of construction and parts illustrated in the accompanying drawings and described hereinabove. The invention is capable of other embodiments and of being practiced in various ways. It is also to be understood that the phraseology or terminology used herein is for the purpose of description and not limitation. Hence, although the present invention has been described hereinabove by way of embodiments thereof, it can be modified, without departing from the spirit, scope and nature of the subject invention as defined in the appended claims.

What is claimed is:

1. A microfluidic device comprising:
a microfluidic flow cell; and
a hydrophilic substrate for being removably interfaced with said microfluidic flow cell for performing a reaction therebetween without any adhesive therebetween, said substrate comprising a flat contiguous surface for removably superimposing said microfluidic flow cell thereon and providing for analyzing a reaction product thereon,
said microfluidic flow cell providing for being removably superimposed on said substrate surface and comprising:
an elongated body defining opposite front and rear ends, opposite lateral sides, a first surface for being interfaced with said substrate surface and an opposite second surface:
at least one reaction portion formed on said first surface at least near said front end and defining with said substrate surface a reaction chamber when said first surface is interfaced with said substrate surface;
a common channel-cavity formed on said first surface and positioned generally centrally of said elongated body and defining with said substrate surface a common channel in fluid communication with said reaction chamber when said first surface is interfaced with said substrate surface;
at least two separate conduit cavities formed on said first surface and defining with said substrate surface respective separate conduits in fluid communication with said common channel and extending therefrom towards a respective one of said opposite lateral sides and towards said rear end when said first surface is interfaced with said substrate surface for providing fluids therein to move both forwardly relative to said rear end and inwardly relative to said lateral side;
at least two separate fluid receiving portions having respective openings formed on said second surface and positioned at least near said rear end for receiving a fluid therein, each said fluid receiving portion being in fluid communication with a respective said conduit;
a valve cavity formed on said first surface and defining a valve with said substrate surface in fluid communication with said common channel and with said conduits when said first surface is interfaced with said substrate surface, said valve being positioned relative to the length of said common channel downstream of said fluid receiving portions; and
a dispensing portion in fluid communication with said reaction chamber, and with the external environment of said microfluidic flow cell, said dispensing portion comprising a dispensing channel formed within said microfluidic flow cell;
wherein when said microfluidic flow cell and said substrate are interfaced, said microlfuidic device is adapted, when submitted to centrifugal forces to allow for the fluid in each said fluid-receiving portion to flow to said reaction chamber and for excess fluid in said reaction chamber to flow into the external environment via said dispensing portion, wherein said valve is configured to burst at a predetermined rotation speed and wherein when the reaction is completed, said microfluidic flow cell being so removable from said substrate so as to allow the reaction product to remain on said substrate.

2. The microfluidic device according to claim 1, wherein said reaction portion comprises a reaction cavity.

3. The microfluidic device according to claim 2, wherein said cavity comprises a structure selected from the group consisting of indentations and at least one groove.

4. The microfluidic device according to claim 1, wherein said fluid-receiving portion comprises a reagent chamber, said fluid comprising a reagent.

5. The microfluidic device according to claim 1, wherein said microfluidic flow cell further comprises a plurality of separate fluid-receiving portions, each said fluid-receiving portion of said plurality being in fluid communication with a common channel, said common channel being in communication with said reaction chamber.

6. The microfluidic device according to claim 1, wherein said dispensing portion comprises a dispensing channel, said microfluidic flow cell further comprising a dispensing channel-cavity, said dispensing channel-cavity defining said dispensing channel when interfaced with said substrate.

7. The microfluidic device according to claim 1, wherein said microfluidic flow cell comprises hydrophobic material.

8. The microfluidic device according to claim 1, wherein said microfluidic flow cell comprises elastomeric material.

9. The microfluidic device according to claim 8, wherein said elastomeric material comprises PDMS.

10. The microfluidic device according to claim 1, wherein said substrate is functionalized to allow for the binding of probes thereon.

11. The microfluidic device according to 1, wherein said substrate comprises glass.

12. The microfluidic device according to claim 1, wherein said substrate comprises a microarray.

13. The microfluidic device according to claim 12, wherein said microarray comprises bioprobe spots.

14. The microfluidic device according to claim 1, wherein said microfluidic flow cell further comprises at least one vent, said vent being in fluid communication with the ambient environment and with said reaction chamber.

15. The microfluidic device according to claim 1, wherein said microfluidic flow cell further comprises at least one vent, said vent being in fluid communication with the ambient environment and with said fluid-receiving portion.

16. The microfluidic device according to claims 1, wherein said microfluidic flow cell further comprises at least one vent, said vent being in fluid communication with the ambient environment and with said conduit.

17. The microfluidic device according to claim 1, wherein said microfluidic flow cell further comprises at least one vent, said vent being in fluid communication with the ambient environment and with said valve.

18. The microfluidic device according to claim 1, wherein said microfluidic flow cell further comprises at least one vent, said vent being in fluid communication with the ambient environment and with said common channel.

19. The microfluidic device according to claim 5, wherein said microfluidic flow cell further comprises at least one vent, said vent being in fluid communication with the ambient environment and with said common channel.

20. The microfluidic device according to claim 1, wherein said microfluidic flow cell further comprises at least one vent, said vent being in fluid communication with the ambient environment and with said dispensing portion.

21. The microfluidic device according to claim 1, further comprising:
a second pair of conduit cavities formed on said first surface and defining with said substrate surface respective second separate conduits in fluid communication with said common channel and extending therefrom towards a respective one of said opposite lateral sides and towards said rear end when said first surface is interfaced with said substrate surface for providing fluids therein to move both forwardly relative to said rear end and inwardly relative to said lateral sides;
at second pair of separate fluid receiving portions having respective openings formed on said second surface and positioned at least near said rear end for receiving a fluid therein, each said fluid receiving portion of said second pair being in fluid communication with a respective said second conduit;
a second valve cavity formed on said first surface and defining a second valve with said substrate surface in fluid communication with said common channel and with said conduits when said first surface is interfaced with said substrate surface, said second valve being positioned relative to the length of said common channel downstream of said fluid receiving portions.

22. The microfluidic device according to claim 21, wherein said second valve is positioned downstream relative to said valve along said common channel.

23. The microfluidic device according to claim 21, wherein said second valve is positioned upstream relative to said valve along said common channel.

24. The microfluidic device according to claim 21, wherein said valve and said second valve are burst at different rotational speeds.

\* \* \* \* \*